United States Patent [19]
Buchman et al.

[11] Patent Number: 4,605,749
[45] Date of Patent: Aug. 12, 1986

[54] PRODUCTION OF ALDEHYDES

[75] Inventors: Ouri Buchman; Ilan Pri-Bar, both of Omer, Israel

[73] Assignee: State of Israel, Prime Minister's Office, Atomic Energy Commission, Beer-Sheva, Israel

[21] Appl. No.: 746,952

[22] Filed: Jun. 20, 1985

[51] Int. Cl.$^4$ ............................................. C07C 45/49
[52] U.S. Cl. ..................................... 549/70; 568/428;
568/490; 568/420; 568/449; 568/423; 568/424;
562/459; 562/508; 562/606; 564/502;
564/305.1; 549/483; 549/498; 549/436;
546/314; 544/335; 558/515; 558/40; 558/434
[58] Field of Search ............... 568/428, 490, 420, 449,
568/423, 424; 562/459, 508, 606; 564/502, 305,
1; 549/70, 483, 498, 436; 546/314; 544/335;
260/465 R, 465.1, 464

[56] References Cited

U.S. PATENT DOCUMENTS 3,960,932 6/1976 Heck ................................ 568/428 X
4,338,467 7/1982 Takano et al. ...................... 568/428

OTHER PUBLICATIONS

Pri-Bar et al., Chem. Abs. vol. 101 (1984) 170,844z.

Primary Examiner—Bernard Helfin
Attorney, Agent, or Firm—Stiefel, Gross, Kurland & Pavane

[57] ABSTRACT

There is provided a process for the production of aldehydes wherein an organic halide is reacted with carbon monoxide at a superatmospheric pressure in the presence of a hydrogen donor and in the presence of a base and of a catalyst in a solvent system.

Catalysts of choice are transition metal catalysts. A preferred temperature range is from about 50° to 150° C.

9 Claims, No Drawings

PRODUCTION OF ALDEHYDES

FIELD OF THE INVENTION

There is provided a method for the production of aldehydes by the formylation of organic halides in the presence of a transition metal catalyst. The process of the invention is effected in the presence of a hydrogen donor, and at a comparatively low pressure of carbon monoxide, superatmospheric,—up to about 10 atmospheres, and preferably up to 3 atmospheres.

BACKGROUND OF THE INVENTION

The carbonylation of organic halides in the presence of transition metal catalysts, and especially of palladium type catalysts is well known. Hitherto this has been used for the synthesis of esters, amides and ketones, as well as of carboxylic acid derivatives. It is known to prepare aldehydes, but this has been done hitherto under a high pressure of carbon monoxide and hydrogen, Yoshida et al, Bull Chem Soc. Japan, 1976 49, 1681 and Schoenberg & Heck, JACS 1974, 96, 7761. The requirement of pressures of the order of 1500 psi and use of high-pressure reaction vessels is a considerable drawback. The present invention overcomes to a large extent the above drawbacks and provides a simple process which can be carried out under convenient conditions of reaction.

SUMMARY OF THE INVENTION

In general terms, the reaction of the invention is one of carbonylation of organic halides in the presence of a suitable transition metal catalyst, a hydrogen donor and a base capable of transferring hydrogen to the catalyst under a comparatively low pressure of carbon monoxide. The superatmospheric pressure is up to 10 atmospheres, and generally up to 3 atmospheres.

The use of gaseous hydrogen is obviated, and there is used a suitable hydrogen donor which is soluble in the reaction mixture. The reaction is one of high chemoselectivity. In general terms the reaction of the invention may be presented by the reaction scheme:

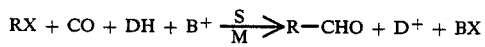

Where R—X designates an organic halide, DH designates a hydrogen donor soluble in the solvent used as reaction medium, or which is gradually dissolved as the reaction takes place, and which is capable of transferring hydrogen to the catalyst; M represents a transition metal catalyst, generally of the palladium or cobalt containing type. Advantageously the catalyst is one which is soluble in the reaction mixture, B+ designates a base which reacts with the hydrogen halide formed during the reaction, S is a suitable solvent or solvent mixture.

The moiety R is of very general nature: it can be a hydrocarbyl group of practically any nature. More specifically, R can be an aliphatic, araliphatic, aromatic, heterocyclic or polycyclic moiety. It can be linear or branched alkyl, cycloalkyl, heterocyclyl, aralkyl, aryl, or polyaromatic group. Such a group may be substituted by one or more identical or different non-interfering substituents. Amongst these there may be mentioned alkyl, hydroxy, alkoxy, carboxy, nitro, isonitrilo, halogen, organic amine (secondary or tertiary), etc. Suitable hydrogen donors used were poly (methylhydrosiloxane) (PMHS) and trialkylhydrosilanes, various salts of formic acid, such as sodium formate, and the like.

Suitable catalysts are of the type of compounds and complexes of palladium, cobalt and other metals. There were tried and found suitable: palladium tetrakis (triphenylphosphine), or compounds with ligands, such as $Ph_2PCH_2CH_2PPh_2$, $(p-CH_3C_6H_5)_3P$, $Et_3P$, etc., palladium diacetate, benzyl-bis(triphenylphosphine) palladium (II) dichloride, tricarbonyl (triphenylphosphine)-cobalt dimer, and the like.

The solvent S used is of the type of acetonitrile, dimethylsulfoxide, HPMA, DMF, formamide etc., or a mixture of any of these.

The base B+ is any suitable base adapted to bind the liberated hydrogen halide; there may be used bases such as HMPA, pyridine, tribenzylamine and the like.

Amongst suitable moieties R of the RX compound used as starting material there may be mentioned alkyl such as methyl, ethyl, propyl, isopropyl, butyl in its various forms, pentyl, hexyl etc. Amongst cycloalkyl there may be mentioned cyclopropyl, and other cycloalkyls of a higher number of carbon atoms; aryl such as phenyl, naphthyl; polyaromatic groups, heterocyclyl such as furyl, furfuryl, pyridyl, pyrimidyl, etc. Amongst aromatic groups used there may be mentioned phenyl substituted by one or more halogens such as iodine, bromine, chlorine, toluene substituted in a similar manner, xylene, indene, naphthalene, methylnaphthalene, diphenyl, acenaphthene, fluorene, phenantrene, anthracene, pyrene, chrysene, thiophene, pyridine, picoline, quinoline, isoquinoline, quinaldine, indole, acridine, carbazole, etc. substituted in a similar manner.

The reaction is generally carried out by providing a suitable reaction mixture as defined above. The reaction is a selective one, and by a choice of suitable conditions it is possible to selectively formylate bromoiodoarenes and chlorobromoarenes at one position only.

The reaction is generally performed in a sealed pressure reaction vessel at a pressure of 1 to 10 atmospheres, but generally a pressure of 1 to 3 atmospheres is adequate. The process of the invention is effected at an elevated temperature, generally in the range of 60° to 125° C., but this is not critical, the time of reaction depending on the nature of the reactants, catalyst and conditions of the reaction. The time of reaction varies generally between about 1 to 20 hours, and the termination of the reaction is generally evident by cessation of carbon monoxide consumption. The aldehyde can be subsequently separated and worked up and purified by conventional procedures.

DESCRIPTION OF THE PREFERRED EMBODIMENT

The invention is illustrated by the following examples which are to be construed in a non-limitative manner.

Formylation of iodobenzene with PMHS in MeCN/HMPA

Tetrakis(triphenylphosphine)palladium (50 mg, 0.05 mmol) was placed in the reaction vessel which was then purged with nitrogen. Acetonitrile (20 mL), HMPA (2.5 mL), PMHS (2.0 mL), and iodobenzene (0.5 mL, 4.5 mmol) were introduced via a syringe through a rubber septum into the vessel. The reaction vessel was purged twice with carbon monoxide and then loaded with 50 psi of carbon monoxide at room temperature. The mixture was stirred at 80° C. for 20 h. After 20 h the reaction mixture was cooled to room temperature, ether (100 mL) was added, the mixture was filtered from solid polymer residue, and the volatile solvents were removed (rotoevaporator). The resulting yellow oil was dissolved in 30 mL of ether, washed with three portions of 30 mL of water, dried with MgSO$_4$ and the ether was removed under reduced pressure. n-Hexane (50 mL) was added and the formed precipitate was removed by filtration, followed by evaporation of the n-hexane. Benzaldehyde (310 mg, 3 mmol) was isolated by Kugelrohr distillation. The pot residue consists of an oily material which had only one $^1$H NMR signal at 0.15 ppm (Si—CH$_3$).

Formylation of bromobenzene in MeCN/Me$_2$SO solution, with PMHS

A mixture of 150 mg (0.15 mmol) of Pd(PPh$_3$)$_4$ and 2.65 g of tribenzylamine (9.2 mmol) was placed in the reaction vessel. After the mixture was purged with nitrogen acetonitrile (10 mL), Me$_2$SO (10 mL), PMHS, and bromobenzene (0.5 mL), 4.5 mmol) were introduced via a syringe through a rubber septum. Carbon monoxide (50 psi) was added at room temperature and the sealed reaction vessel was heated to 110° C. for 18 h. After workup as described before, 300 mg (2.8 mmol) or benzaldehyde were separated by Kugelrohr distillation.

Formylation of bromobenzene with sodium formate as the hydrogen donor

A mixture of 50 mg (0.05 mmol) of Pd(PPh$_3$)$_4$ and 400 mg (6 mmol) of sodium formate was placed in the reaction vessel.

After the mixture was purged with nitrogen, acetonitrile (4 mL), dimethyl sulfoxide (4 mL), and bromobenzene (0.1 mL, 0.95 mmol) were added via a syringe through a rubber septum. Carbon monoxide (50 psi) was introduced at room temperature and the sealed reaction vessel was heated to 125° C. After 18 h the reaction mixture was cooled to room temperature, methanol (30 mL) was added, and benzaldehyde (63.7 mg, 0.60 mmol) was determined by HPLC in the crude filtered methanol solution.

TABLE I

Formylation of Aromatic Halides with PMHS as a Hydrogen Donor

| Entry | Halide (mmol) | Catalyst (mmol) | Base (mmol) | PMHS mL | Reactn temp. °C. | Product[b] (% yield) |
|---|---|---|---|---|---|---|
| 1 | C$_6$H$_6$I (5.0) | Pd(PPh$_3$)$_4$ (0.05) | HMPA (15) | 2.0 | 80[c] | C$_6$H$_5$CHO (96) (68)[d] |
| 2 | 4-BrC$_6$H$_4$I (1.0) | Pd(PPh$_3$)$_4$ (0.01) | HMPA (3) | 0.4 | 80[c] | 4-BrC$_6$H$_4$CHO (95) |
| 3 | C$_6$H$_5$Br (1.0) | Pd(PPh$_3$)$_4$, (0.03) | (C$_6$H$_5$CH$_2$)$_3$N (1.4) | 0.4 | 110 | C$_6$H$_5$CHO (59) |
| 4 | 4-ClC$_6$H$_4$Br (1.0) | Pd(PPh$_3$)$_4$ (0.03) | (C$_6$H$_5$CH$_2$)$_3$N (1.4) | 0.4 | 110 | 4-ClC$_6$H$_4$CHO (54) |
| 5 | 2-CH$_3$C$_6$H$_4$I (1.0) | Pd(PPh$_3$)$_4$ (0.03) | (C$_6$H$_5$CH$_2$)$_3$N (1.4) | 0.4 | 110 | 2-CH$_3$C$_6$H$_4$CHO (23) |
| 6 | 2-CH$_3$C$_6$H$_4$Br (1.0) | Pd(PPh$_3$)$_4$ (0.03) | (C$_6$H$_5$CH$_2$)$_3$N (1.4) | 0.4 | 110 | 2-CH$_3$C$_6$H$_4$CHO (2) |
| 7 | 4-CH$_3$C$_6$H$_4$Br (1.0) | Pd(PPh$_3$)$_4$ (0.03) | (C$_6$H$_5$CH$_2$)$_3$N (1.4) | 0.4 | 110 | 4-CH$_3$C$_6$H$_4$CHO (48) |
| 8 | 2-CH$_3$OC$_6$H$_4$Br (1.0) | Pd(PPh$_3$)$_4$ (0.03) | (C$_6$H$_5$CH$_2$)$_3$N (1.4) | 0.4 | 110 | 2-CH$_3$OC$_6$H$_4$CHO (14) |
| 9 | 4-CH$_3$OC$_6$H$_4$Br (1.0) | Pd(PPh$_3$)$_4$ (0.03) | (C$_6$H$_5$CH$_2$)$_3$N (1.4) | 0.4 | 110 | 4-CH$_3$OC$_6$H$_4$CHO (35) |
| 10 | C$_6$H$_5$CH$_2$Br (5.0) | Pd(PPh$_3$)$_4$ (0.15) | (C$_6$H$_5$CH$_2$)$_3$N (7.0) | 2.0 | 110 | C$_6$H$_5$CH$_2$CHO (36)[d] |
| 11 | 1-bromonaphthalene (1.0) | Pd(PPh$_3$)$_4$ (0.03) | (C$_6$H$_5$CH$_2$)$_3$N (1.4) | 0.4 | 125 | 1-naphthaldehyde (61) |
| 12 | 2-bromothiophene (1.0) | Pd(PPh$_3$)$_4$ (0.03) | (C$_6$H$_5$CH$_2$)$_3$N (1.4) | 0.4 | 125 | 2-thiophene-carboxaldehyde (82) |
| 13 | 4-NCC$_6$H$_4$Br (1.0) | Pd(PPh$_3$)$_4$ (0.03) | (C$_6$H$_5$CH$_2$)$_3$N (1.4) | 0.4 | 125 | 4-NCC$_6$H$_4$CHO (48) |
| 14 | C$_6$H$_5$I (1.0) | Pd(OAc)$_2$ (0.1) | (C$_6$H$_5$CH$_2$)$_3$N (1.4) | 0.4 | 110 | C$_6$H$_5$CHO (95) |
| 15 | C$_6$H$_5$Br (1.0) | PhCH$_2$PdCT(PPh$_3$)$_2$ | (C$_6$H$_5$CH$_2$)$_3$N (1.4) | 0.4 | 110 | C$_6$H$_5$CHO (69) |
| 16 | C$_6$H$_5$I (1.0) | PdCl$_2$(PPh$_3$)$_2$, 3% on polymer (first run) | (C$_6$H$_5$CH$_2$)$_3$N (1.4) | 0.4 | 110 | C$_6$H$_5$CHO (85) |
| 17 | C$_6$H$_5$I (1.0) | PdCl$_2$(PPh$_3$)$_2$, 3% on polymer (2nd run) | (C$_6$H$_5$CH$_2$)$_3$N (1.4) | 0.4 | 110 | C$_6$H$_5$CHO (94) |
| 18 | C$_6$H$_5$I (1.0) | (Co(CO)$_3$PPh$_3$)$_2$ (0.03) | (C$_6$H$_5$CH$_2$)$_3$N (1.4) | 0.4 | 110 | C$_6$H$_5$CHO (18) |
| 19 | C$_6$H$_5$I (1.0) | Pd(PPh$_3$)$_4$ (0.03) | (C$_6$H$_5$CH$_2$)$_3$N (1.4) | 0.4 | 110 | C$_6$H$_5$CHO (96) |
| 20 | C$_6$H$_5$I (1.0) | Pd(PPh$_3$)$_4$ (0.03) | pyridine (2.0) | 0.4 | 110 | C$_6$H$_5$CHO (16) |
| 21 | C$_6$H$_5$I (1.0) | Pd(PPh$_3$)$_4$ (0.03) | H$_3$CN(Oct$_2$ (2.0) | 0.4 | 110 | e |
| 22 | C$_6$H$_5$I (1.0) | Pd(PPh$_3$)$_4$ (0.03) | Ca(OH)$_2$ (2.0) | 0.4 | 110 | e |
| 23 | C$_6$H$_5$Cl (1.0) | Pd(PPh$_3$)$_4$ (0.03) | (C$_6$H$_5$CH$_2$)$_3$N (1.4) | 0.4 | 110 | e |

[a]CO initial pressure 50 psi; reaction time 18 h.
[b]Yields determined by GC or HPLC unless otherwise stated.
[c]Reaction time 20 h.
[d]Isolated yield.
[e]No reaction.

TABLE II

Formylation of Aryl Halides with Sodium Formate as the Hydrogen Donor

| Entry | Halide (mmol) | Catalyst (mmol) | Sodium formate (mmol) | Product[b] (% yield) |
|---|---|---|---|---|
| 1 | C$_6$H$_5$I (1.0) | Pd(PPh$_3$)$_4$ (0.03) | 6.0 | C$_6$H$_5$CHO (72) |
| 2 | C$_6$H$_5$I (1.0) | Pd(PPh$_3$)$_4$ (0.04) | 10.0 | C$_6$H$_5$CHO (80) |
| 3 | C$_6$H$_5$Br (1.0) | Pd(PPh$_3$)$_4$ (0.03) | 6.0 | C$_6$H$_5$CHO (45) |
| 4 | C$_6$H$_5$Br (1.0) | Pd(PPh$_3$)$_4$ (0.04) | 10.0 | C$_6$H$_5$CHO (58) |
| 5 | C$_6$H$_5$Cl (1.0) | Pd(PPh$_3$)$_4$ (0.05) | 6.0 | c |

[a]Carbon monoxide initial pressure 50 psi at room temperature; reaction temperature 125° C.; reaction time 18 h.
[b]Yields determined by HPLC.
[c]No reaction.

We claim:
1. A process for the production of aldehydes of the general formula

R—CHO

wherein R designates an aliphatic, aromatic, araliphatic, polycyclic, or heterocyclic group which may be substituted by one or more identical or different non-interfering substituents, which comprises reacting an organic halide of the formula

R—X where R is as defined above and X is an iodine or bromine atom, with carbon monoxide at a superatmospheric pressure, of up to about 10 atmospheres and at a temperature of from 50° to 150° C., in a reaction mixture containing:
(a) a catalyst consisting of a palladium or cobalt metal compound or complex soluble in the reaction mixture;
(b) a hydrogen donor capable of transferring hydrogen in the reaction mixture, selected from the group consisting of poly (methylhydrosiloxanes), trialkylhydrosilanes and formic acid salts; and
(c) a base which reacts with hydrogen halide formed during the reaction.

2. A process according to claim 1, wherein R is alkyl, cycloalkyl, aryl, aralkyl, alkaryl, polycyclyl, heterocyclyl which may be substituted by one or more identical or different substituents selected from alkyl, hydroxy, alkoxy, carboxy, nitro, nitrile, isonitrile, halogen, secondary or tertiary amine.

3. A process according to claim 1, wherein the catalyst is selected from palladium tetrakis (triphenylphosphine); a palladium compound with a ligand selected from $Ph_2PCH_2CH_2PPh_2$, $(p-CH_3C_6H_5)_3P$ and $Et_3P$; palladium diacetate, benzylbis(triphenylphosphine)palladium (II) dichloride; and tricarbonyl (triphenylphosphine) cobalt dimer, 4. A process according to claim 1, wherein the reaction is carried out in a solvent selected from acetonitrile, dimethyl sulfoxide, HMPA, DMF and formamide, and mixtures thereof.

5. A process as claimed in claim 1, wherein the base is HMPA, pyridine or an organic amine.

6. A process according to claim 1 wherein the hydrogen donor is poly(methylhydrosiloxane).

7. A process according to claim 1 wherein the hydrogen donor is a salt of formic acid.

8. The process of claim 1 wherein the reactant (RX) is bromobenzene, 4-bromoanisole, 4-bromoveratrole, 3,4-methylenedioxybromobenzene, 2-bromothiophene, or 3-bromothiophene, and the product is benzaldehyde, anisaldehyde, veratraldehyde, piperonal, 2-thiophenealdehyde or 3-thiophenealdehyde, respectively.

9. The process according to claim 1 wherein the reaction is carried out for a period of from 1 to 20 hours.

* * * * *